United States Patent [19]

Deniega

[11] Patent Number: 4,598,711

[45] Date of Patent: Jul. 8, 1986

[54] SURGICAL INSTRUMENT

[75] Inventor: Jose C. Deniega, Brookfield, Conn.

[73] Assignee: American Cyanamid Company, Stamford, Conn.

[21] Appl. No.: 639,272

[22] Filed: Aug. 9, 1984

[51] Int. Cl.$^4$ ............................................. A61B 17/12
[52] U.S. Cl. ...................... 128/326; 72/410; 227/DIG. 1
[58] Field of Search .............. 128/326, 325, 337, 346; 227/DIG. 1, 19, 120; 29/243.56; 72/410

[56] References Cited

U.S. PATENT DOCUMENTS 4,185,762  1/1980  Froehlich ........................... 227/120

FOREIGN PATENT DOCUMENTS 68046    1/1983  European Pat. Off. ............ 128/326
7234     1/1983  Japan .................................. 128/326
8202825  9/1982  PCT Int'l Appl. .................. 128/325

Primary Examiner—Robert Peshock
Assistant Examiner—Cary E. Stone
Attorney, Agent, or Firm—Charles F. Costello, Jr.

[57] ABSTRACT

An improved surgical instrument is described. The instrument comprises a housing. The housing has a handle for activating a force, and a link for translating the force. The instrument also comprises a probe. The probe has jaws or an anvil for holding a single wound closure element, a movable crimp bar for crimping the single closure element in the jaw or anvil, the proximal end of the crimp bar being connected to the distal end of the link, a spring for advancing a plurality of wound closure elements, and an injector for loading a single wound closure element, from the plurality, into the jaws or onto the anvil. The improvement comprises the link indirectly connected to the spring and the injector to integrally effect the crimp bar, spring and injector.

The surgical instrument can be a ligating instrument.

6 Claims, 12 Drawing Figures

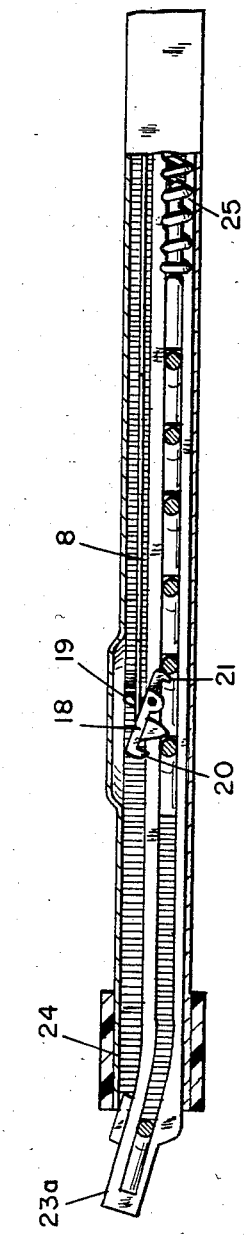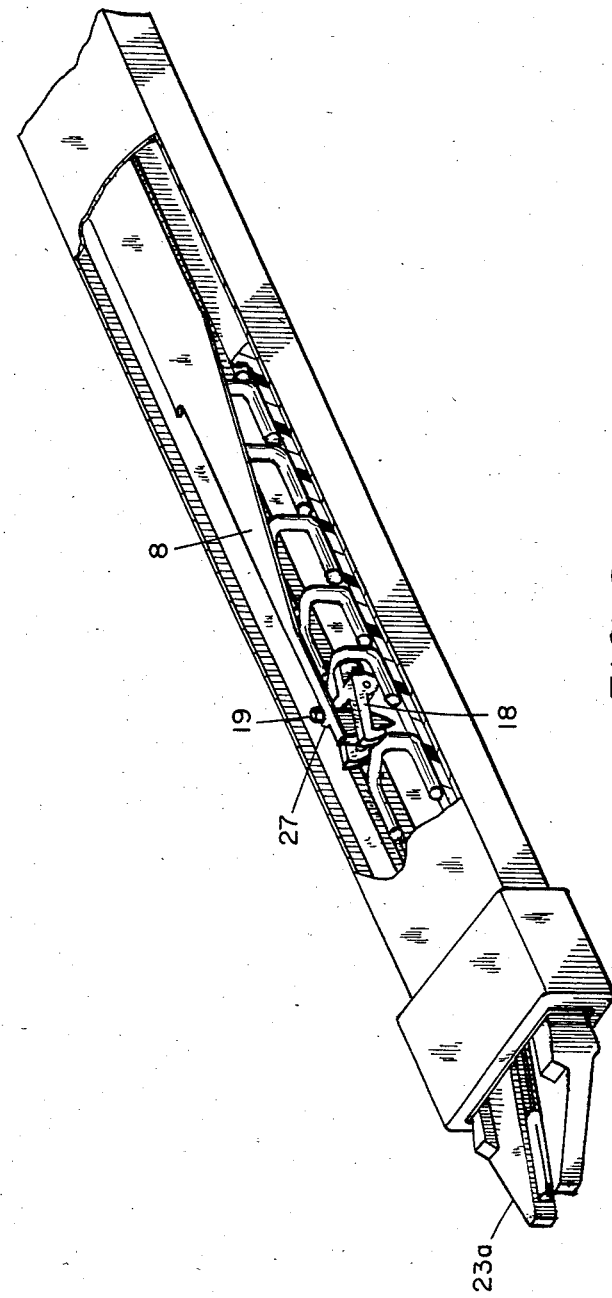
FIG. 5
FIG. 6

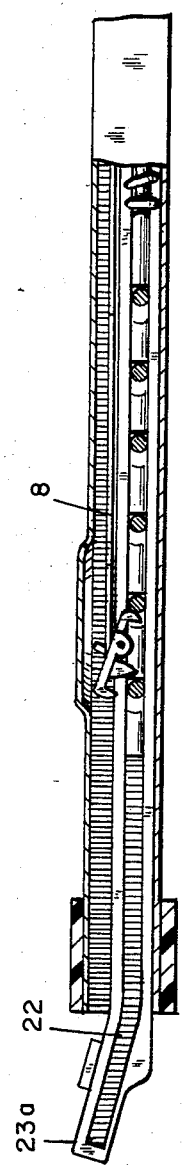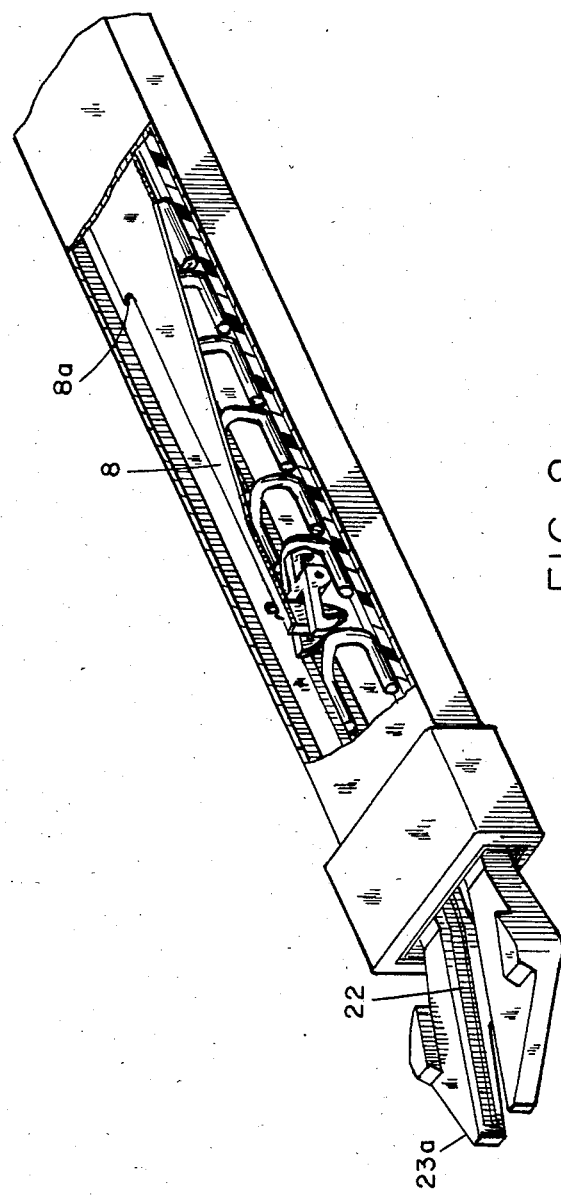
FIG. 7
FIG. 8

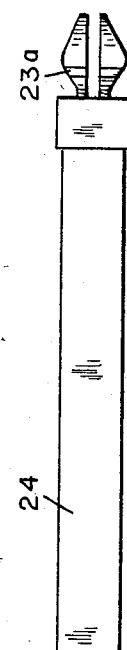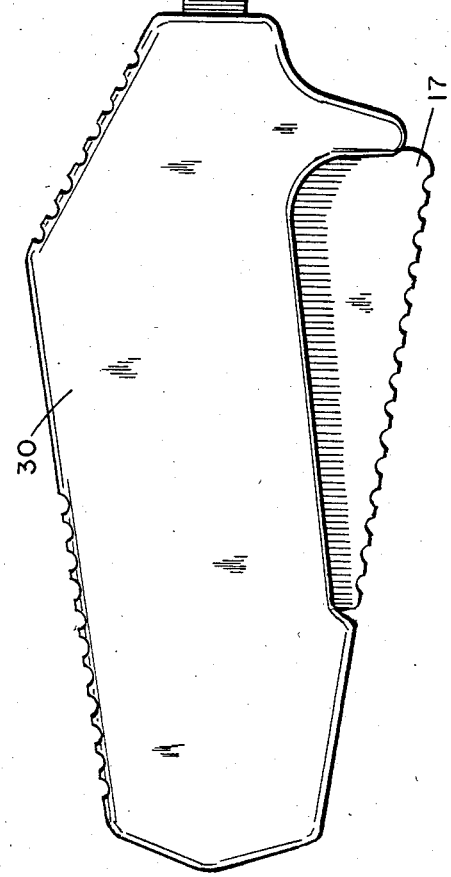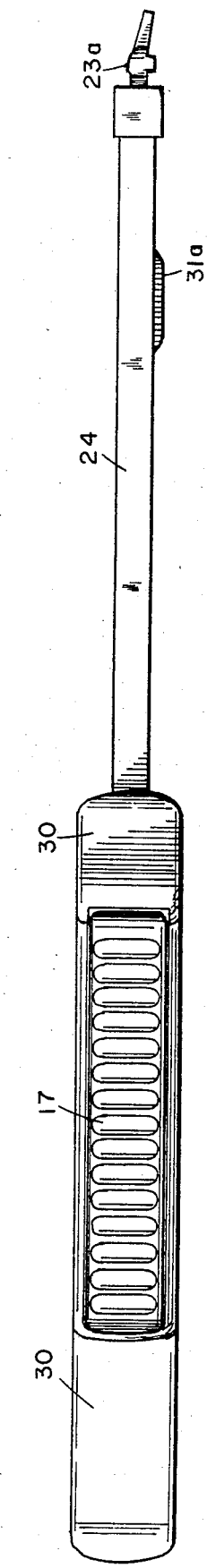
FIG. 9
FIG. 10
FIG. 11

SURGICAL INSTRUMENT

This invention relates to an improved surgical ligating instrument. The improvement relates to means for translating a force. The improved translating means integrally effect means for crimping single wound closure element, means for advancing a plurality of wound closure elements, and means for loading the single wound closure element.

An improved surgical instrument has been invented. The instrument comprises a housing. The housing has means for activating a force, and means for translating the force. The instrument also comprises a probe. The probe has means for holding a single wound closure element, means for crimping the single closure element in the holding means, means for advancing a plurality of wound closure elements, and means for loading a single wound closure element, from said plurality, into said holding means.

The improvement comprises the translating means integrally effecting the crimping, advancing and loading means.

In the description of this invention, the term wound closure element is intended to be generic and to include any type of closure element which can approximate mammalian tissue. As such, the term wound closure element includes, but is not necessarily limited to, a clamp, clip, staple, hook, button and snap. A ligating clip and a surgical staple are embodied in the detailed description below. The term mammalian tissue (to be approximated) is also intended to be generic and includes, but is not necessarily limited to, internal tissue such as an intestine or an artery, or external tissue such as the skin or fascia.

One embodiment of the surgical instrument of this invention is an improved surgical ligating instrument. The housing of the ligating instrument has means for activating a force, and means for translating the force. The ligating instrument also comrises a probe. The probe has means for crimping a single ligating clip, means for advancing a plurality of ligating clips, the distal end of the advancing means having a pair of jaws, and means for loading a single clip, from the plurality, into the jaws.

The improvement to the ligating instrument comprises the translating means integrally effecting the crimping, advancing and loading means.

Another embodiment of the surgical instrument of this invention is an improved surgical stapler. The housing of the stapler has means for activating a force, and means for translating the force. The stapler also comprises a probe. The probe has means for holding a single staple, means for crimping the single staple on the holding means, means for advancing a plurality of staples, and means for loading a single staple, from the plurality, onto the holding means.

The improvement to the stapler comprises the translating means integrally effecting the crimping, advancing and loading means.

The activating means of the improved surgical instrument, e.g. the ligating instrument and the stapler, can comprise a sole element. In one embodiment, the sole activating means is a handle. In another embodiment, the sole activating means is a trigger.

The translating means of the improved surgical instrument, e.g. the ligating instrument and the stapler, can comprise a link. The proximal end of the link is adjacent the activating means. The distal end of the link is connected to the crimping means. Between the proximal and distal ends, the link is indirectly connected to the advancing and loading means.

In yet another embodiment, the crimping means of the improved surgical instrument, e.g. the ligating instrument and the stapler, can comprise a movable crimp bar. The proximal end of the movable crimp bar is connected to the above described link. In the ligating instrument, the distal end of the movable crimp bar is adjacent to the pair of jaws.

In a specific embodiment of the surgical instrument, e.g. the ligating instrument and the stapler, the crimp bar has a biasing member. In a more specific embodiment, the biasing member is a spring adjacent the proximal end of the crimp bar.

In a further embodiment of the surgical stapler, the holding means comprise a pair of jaws. The jaws are contained on the distal end of the advancing means.

DESCRIPTION OF THE DRAWINGS

FIGS. 5 and 6 are broken and partially cut-away bottom and perspective views, respectively, of FIG. 4 showing the location of the loading, clip advancing and crimping means;

FIGS. 7 and 8 are broken and partially cut-away bottom and perspective views, respectively, showing the location of the loading, clip advancing and crimping means of the activating and translating means of FIG. 4 have partially returned to their rest position;

FIG. 9 is a top plan view of the instrument of this invention;

FIG. 10 is a side elevation of FIG. 10; and

FIGS. 11 and 12 are bottom and back plan views, respectively, of FIG. 10.

DETAILED DESCRIPTION

Figure 1:
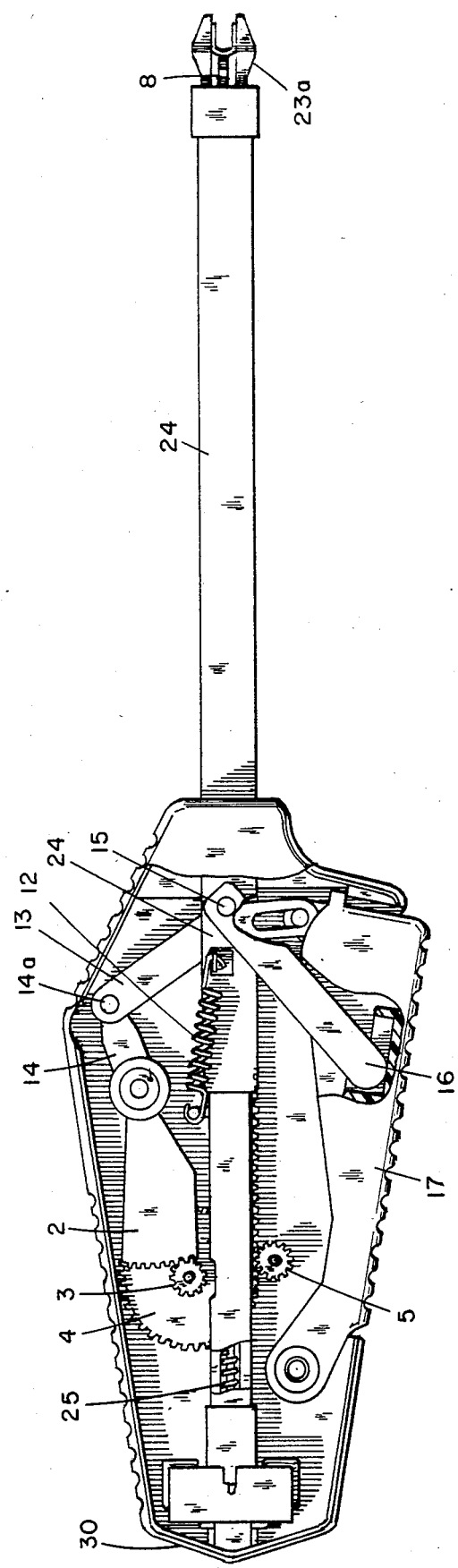
FIG. 1 is a partially cut-away side view showing the activating and translating means in the housing in a rest position.
Figure 2:
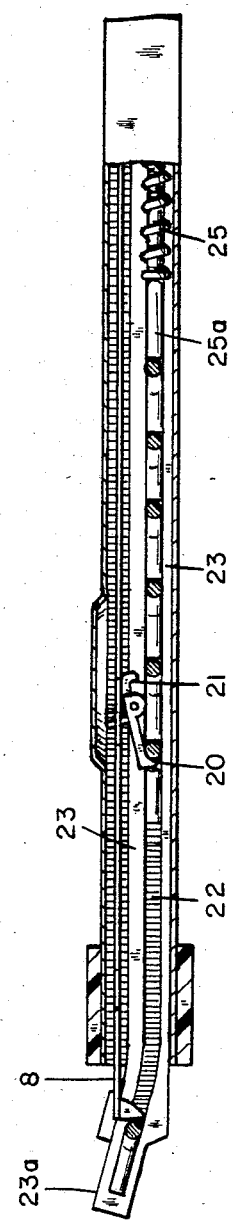
FIGS. 2 and 3 are broken and partially cut-away bottom and perspective views, respectively, of FIG. 1 showing the loading, clip advancing and crimping means.
Figure 3:
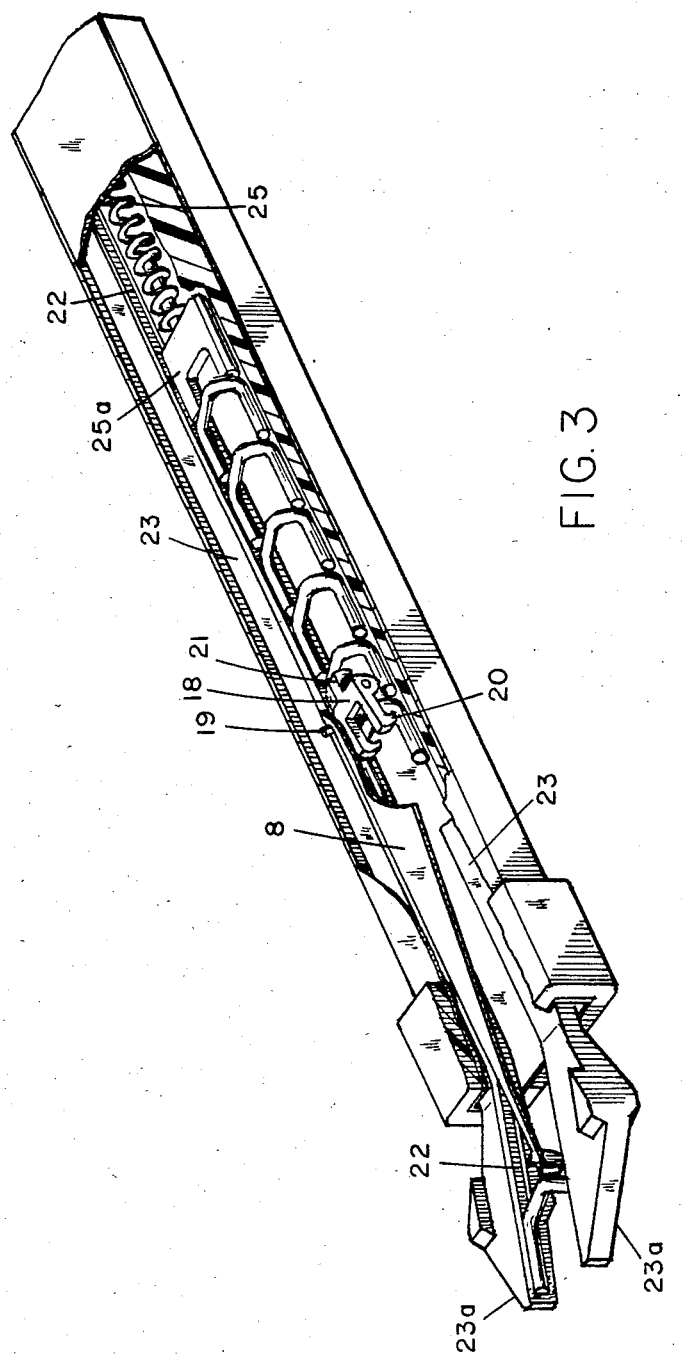

Referring to FIGS. 1 to 3, clip injector 8 is rigidly attached to rack 6 (the gear teeth on the bottom of rack 6 are shown in FIGS. 1). Alternatively, injector 8 can be manufactured as one part with the rack 6 contained on the proximal end.

Reduction gears 3 and 4 are keyed togther to form a gear cluster. Alternatively, gears 3 and 4 can be manufactured as one part. Sector gear 2 meshes with gear 3, and gear 4 meshes with pinion gear 5. Gear 5 meshes with the gear teeth of rack 6.

Spring 25 is compressed between a pusher 25a and the (internal) back of the housing 30. The pusher 25a can be a plastic part and serves as the interface between the rearmost clip and spring 25. That is, the rearmost clip of a column of clips is adjacent the pusher; the spring 25 is applying a constant force to urge the plurality of clips forward.

The plurality of clips are contained in a pair of internal slots 22 that run throughout the length of the pair aligned members 23. The distal end of the members 23 contain jaws 23a.

The gears 2 to 5 and the mechanical elements contained by the crimp bar 24 are known from the prior art. See, e.g. European patent application No. 68,046 published Jan. 5, 1983 entitled "Surgical Ligating Instrument", which is incorporated herein by reference.

The load lever 14 which has a sector gear 2 is carried by the motion of link 13 through pin 14a. The link 16 is contained on pin 15 and rides on the motion of handle 17. The link 16 is essentially simultaneously activated by a force supplied to the handle 17.

As shown in FIGS. 1 to 3, a clip is in the jaws 23a with the instrument in its initial rest position.

Figure 4:
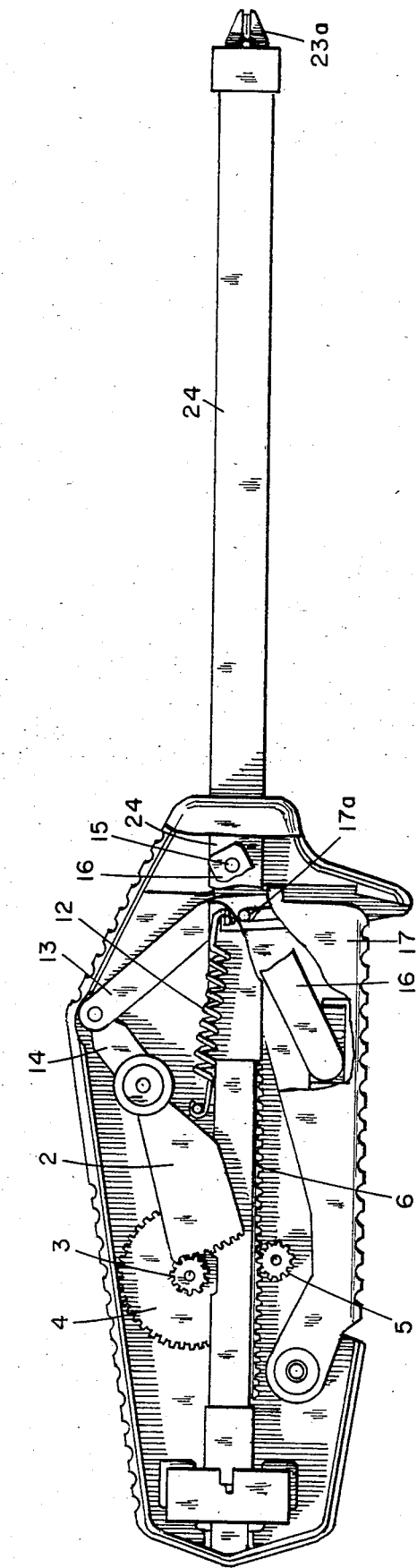
FIG. 4 is a partially cut-away side view showing the activating and translating means of FIG. 1 in a fully compressed position.
Figure 12:
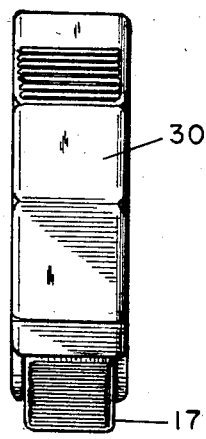

Referring specifically to FIGS. 4 to 6, as the crimp bar handle 17 is being compressed, crimp bar 24 is pushed forward by the pin 15, through link 16. The front end of the crimp bar 24 cams on the incline planes of the jaws 23a. The camming causes the two jaws to come together crimping the clip.

Referring to FIG. 4, as the crimp bar handle 17 approaches about two-thirds to three-quarters of a complete compression, pin 17a contacts and then begins to move link 13. This causes link 13 to act on 14. Through the gears 2 through 5 (more fully described above), the rack 6 slides back pulling with it the injector 8.

As shown in FIGS. 4, 5 and 6, tab 27 hits stem 19, pivoting clip actuator 18. This drops pawl 21 to hold back the column of clips that is being urged forward by spring 25, and lifts pawl 20 to clear the path for the lead noncrimped clip. The front end of the clip injector 8 is flexible such that it cams over and gets behind the lead clip. The pusher 25a (shown in FIG. 3) can contain an opening such that the flanged portion at the distal end of the injector 8 is held by the opening after the rearmost (final) clip is crimped by the jaws.

In the clip ejected position shown in FIGS. 7 and 8, a narrow gap separates the jaws 23a. The frontmost noncrimped clip opens the jaws during reloading. The jaws can thus hold the clip before crimping, nd also during partial crimping. For example, if the crimp bar handle 17 shown in FIG. 4 is released before complete compression, the partially crimped clip will not fall out of the slots 22 in the jaws 23a.

Referring serially to FIGS. 7 and 8 and then to FIGS. 1, 2 and 3, a single noncrimped clip is pushed to the jaws 23a by the clip injector 8. This is accomplished on the return travel of the handle 17, which reverses the motion of the gears 2 and 5 described in FIG. 4. That is, on relaxing the force on the handle 17, sector gear 2 turns clockwise and cluster gears 3 and 4 counterclockwise. Pinion gear 5 turns clockwise driving rack 6 and clip injector 8 forward. The frontmost clip is thus pushed to the tip of the jaws 23a as fully shown in FIGS. 2 and 3. The crimp bar return spring 12 keeps the crimp bar 24 in a rearward position and the handle 17 in the initial rest position. Through the gears 2 to 6, the crimp bar return spring 12 also holds the injector 8 in its forward position.

Referring specifically to FIG. 8, near the end of the forward stroke of the clip injector 8, a detail 8a (which is shown acting on stem 19 in FIG. 3) on the clip injector pushes the actuator stem 19 causing the actuator 18 to pivot forward.

As more fully shown in FIGS. 2 and 3, this motion of the actuator 18 drops pawl 20 and lifts pawl 21. The column of clips in slots 22 is constantly being urged forward by spring 25. The clips are now free to slide forward until the lead clip is stopped by pawl 20.

Referring to FIGS. 9 to 12, the surgical ligating instrument of this invention has a housing 30. The housing contains a force activating means, for example a handle 17. Referring, e.g., to FIG. 4, the link 16 is directly and the gears 2 to 5 are indirectly activated by the handle 17.

Preferably, the size of the housing 30 is such that a predominant portion of the housing can be essentially held by the palm of the hand. The distal end of the crimp bar 24 contains jaws 23A.

The optional raised portion 31a in FIGS. 9 and 11 accommodates the pivoting clip actuator 18 (see e.g., FIGS. 5 and 6). That is, the crimp bar 24 can be manufactured in a narrower width if the raised portion 31a is used. Finally, the raised portion 31a can be manufactured from a transparent material. If the raised portion is manufactured from a transparent material, it can be used to give a visual identification to the user that clips are, or are not remaining in the instrument.

Referring again to FIGS. 9 to 12, a scalloped configuration in the top and bottom portions of the housing 30 and the handle 17 is preferred. The scalloping assists the user to grip the housing and the handle 17, and to compress the handle into the housing.

The above detailed description of this invention embodies a surgical instrument containing at least one ligating clip. However, it is to be understood that this invention can be used for other wound closure elements, e.g. a surgical staple.

The jaws of the above described instrument can be adapted without undue experimentation to crimp a surgical staple. See, e.g., U.S. Pat. No. 4,375,866 issued Mar. 8, 1983 entitled Skin Clip Applier, which is incorporated herein by reference. Alternatively, the above described instrument may be modified to contain an anvil for crimping a surgical staple. See generally, e.g., U.S. Pat. No. 4,406,392 issued Sept. 27, 1983 entitled Surgical Stapling Instrument, which is also incorporated herein by reference.

What is claimed:

1. A surgical instrument comprising
A. a housing having
  I. a sole means for activating a force, and
  II. a link for translating said force; and
B. a probe having
  I. means for holding a single wound closure element,
  II. a movable crimp bar for crimping said single closure element in said holding means, the proximal end of said crimp bar connected to the distal end of said link,
  III. means for advancing a plurality of wound closure elements, and
  IV. means for loading a single wound closure element, from said plurality, into said holding means, the improvement comprising said link indirectly connected to said advancing and loading means to integrally effect said crimp bar and said advancing and loading means.

2. An instrument of claim 1 wherein said crimp bar has a biasing member.

3. An instrument of claim 2 wherein said biasing member is a spring adjacent the proximal end of said crimp bar.

4. A surgical ligating instrument comprising
A. a housing having
  I. a sole means for activating a force, and
  II. a link for translating said force; and
B. a probe having I. a movable crimp bar for crimping a single ligating clip, the proximal end of said crimp bar connected to the distal end of said link,
II. means for advancing a plurality of ligating clips, the distal end of said advancing means having a pair of jaws, and
III. means for loading a single clip from said plurality into said jaws, the improvement comprising said link indirectly connected to said advancing and loading means to integrally effect said crimp bar and said advancing and loading means.

5. An instrument of claim 4 wherein said crimp bar has a biasing member.

6. An instrument of claim 5 wherein said biasing member is a spring adjacent the proximal end of said crimp bar.

* * * * *